United States Patent
Padinger et al.

(10) Patent No.: US 7,894,644 B2
(45) Date of Patent: Feb. 22, 2011

(54) FINGERPRINTING DEVICE

(75) Inventors: Franz Padinger, St. Marien (AT); Klaus G. Schröter, Berlin (DE)

(73) Assignee: NanoIdent Technologies AG, Linz (AT)

( * ) Notice: Subject to any disclaimer, the term of this patent is extended or adjusted under 35 U.S.C. 154(b) by 1002 days.

(21) Appl. No.: 11/662,326

(22) PCT Filed: Aug. 24, 2005

(86) PCT No.: PCT/AT2005/000336

§ 371 (c)(1),
(2), (4) Date: Mar. 26, 2007

(87) PCT Pub. No.: WO2006/026794

PCT Pub. Date: Mar. 16, 2006

(65) Prior Publication Data

US 2008/0031501 A1 Feb. 7, 2008

(30) Foreign Application Priority Data

Sep. 8, 2004 (AT) .............................. A 1500/2004

(51) Int. Cl.
*G06K 9/00* (2006.01)
*H01L 51/00* (2006.01)
(52) U.S. Cl. ........................................ 382/124; 257/40
(58) Field of Classification Search .................. 382/124
See application file for complete search history.

(56) References Cited

U.S. PATENT DOCUMENTS

| | | | |
|---|---|---|---|
| 4,672,149 A * | 6/1987 | Yoshikawa et al. ........... 136/263 |
| 6,278,127 B1 * | 8/2001 | Dodabalapur et al. ......... 257/40 |
| 6,327,376 B1 | 12/2001 | Harkin | |
| 6,531,711 B2 * | 3/2003 | Sakakura et al. .............. 257/53 |
| 6,606,399 B2 | 8/2003 | Burrows et al. | |
| 6,852,996 B2 * | 2/2005 | Thomas et al. ................ 257/40 |
| 7,141,839 B2 * | 11/2006 | Thomas et al. .............. 257/252 |
| 2003/0090650 A1 * | 5/2003 | Fujieda ........................ 356/71 |
| 2004/0067393 A1 | 4/2004 | Burrows et al. | |
| 2004/0184027 A1 | 9/2004 | Mizutani et al. | |
| 2004/0252867 A1 | 12/2004 | Lan et al. | |

(Continued)

FOREIGN PATENT DOCUMENTS

JP 2004 016407 A 1/2004

(Continued)

OTHER PUBLICATIONS

International Search Report of PCT/AT2005/000337.

(Continued)

*Primary Examiner*—Bhavesh M Mehta
*Assistant Examiner*—Utpal Shah
(74) *Attorney, Agent, or Firm*—Collard & Roe, P.C.

(57) ABSTRACT

Described is a fingerprinting device with a translucent top layer (8) which forms a finger rest and between which and a light-emitting layer (9) a layer (1) of light-sensitive elements is provided in a matrix arrangement, and with an evaluation circuit (7) connected to the light-sensitive elements. In order to provide advantageous design conditions, it is proposed that the layer (1) of light-sensitive elements have a translucent, photoactive layer (2) based on organic semiconductors between two translucent electrode layers (3, 4) consisting of intersecting strip conductors (5, 6).

5 Claims, 1 Drawing Sheet

U.S. PATENT DOCUMENTS

| | | |
|---|---|---|
| 2005/0110055 A1 | 5/2005 | Thomas et al. |
| 2005/0141048 A1 | 6/2005 | Mizutani |

FOREIGN PATENT DOCUMENTS

| | | |
|---|---|---|
| WO | WO 97/36544 A1 | 10/1997 |
| WO | WO 99/39372 A | 8/1999 |
| WO | WO 9939372 A2 * | 8/1999 |
| WO | WO 00/60530 | 10/2000 |
| WO | WO 03/015189 A | 2/2003 |
| WO | WO 2004/036484 A | 4/2004 |

OTHER PUBLICATIONS

Davide Maltoni et al: "Handbook of Fingerprint Recognition." Jun. 2003, Springer, New York, XP 00235896, p. 62. (ISR).

Nalini Ratha Et Ruud Bolle: "Automatic Fingerprint Recognition Systems." Dec. 2003, Springer, New York, XP002358397, pp. 31, 37, 38, 41 and 48. (ISR).

S. Miyata: "Organic Electroluminescent Materials and Devices." 1997, Gordon and Breach, Amsterdam, XP002358398 pp. 391-414. (ISR).

Jospeh Shinar: "Organic Light-Emitting Devices." 2004, Springer, New York, XP002358399 pp. 1-41. (ISR).

C.J. Brabec et al: "Organic Photovoltaics." 2003, Springer, Berline, XP002358400, pp. 1-56. (ISR).

International Search Report.

Lan, J. et al., Fingerprint Imager Based on a-Si:H Active Matrix Photo-Diode Arrays, pp. 419-422.

* cited by examiner

FINGERPRINTING DEVICE

CROSS REFERENCE TO RELATED APPLICATIONS

Applicants claim priority under 35 U.S.C. §119 of Austrian Application No. A 1500/2004 filed Sep. 8, 2004. Applicants also claim priority under 35 U.S.C. §365 of PCT/AT2005/000336 filed Aug. 24, 2005. The international application under PCT article 21(2) was not published in English.

FIELD OF THE INVENTION

The invention relates to a fingerprinting device with a translucent top layer which forms a finger rest and between which and a light-emitting layer a layer of light-sensitive elements is provided in a matrix arrangement, and with an evaluation circuit connected to the light-sensitive elements.

DESCRIPTION OF THE PRIOR ART

In order to be able digitally to record a fingerprint, without firstly optically imaging the fingerprint using a lens system, it is known (WO 97/036544 A1) to arrange light-sensitive elements, preferably photodiodes or phototransistors, using thin-layer technology on a transparent carrier made of glass or quartz and to cover them with a light-emitting layer consisting, for example, of electroluminescent diodes. As the light-sensitive elements are arranged in rows in a matrix and the rows of elements are separated from one another by translucent gaps, light can be cast from the light-emitting layer, through the translucent gaps and the transparent carrier, onto the finger which is positioned, for recording a fingerprint, against the carrier acting as a finger rest. The light, which is reflected differently at the ridges and recesses of the skin, is detected by the light-sensitive elements, the electrical signals of which, which are dependent on the intensity of the reflected light, are transmitted in an elementary manner into an evaluation circuit for producing a digital image of a fingerprint. The main drawback of this known fingerprinting device is the design costs caused by the use of light-sensitive elements based on inorganic semiconductors; in addition, the fingerprint to be recorded can be illuminated merely by comparatively narrow gaps between the light-sensitive elements.

SUMMARY OF THE INVENTION

The object of the invention is accordingly to construct a fingerprinting device of the type described at the outset in such a way as to allow a digital image of a fingerprint to be obtained using simple constructional means.

The invention achieves the object set in that the layer of light-sensitive elements has a translucent, photoactive layer based on organic semiconductors between two translucent electrode layers consisting of intersecting strip conductors.

As the light-sensitive elements are formed by a photoactive layer based on inorganic semiconductors, this photoactive layer can itself be translucent, and this eliminates the restrictions otherwise caused by the non-translucent inorganic semiconductors with regard to the illumination of the fingerprint using a light-emitting layer on the side of the light-sensitive elements that is remote from the finger rest. There are also comparatively low production costs based firstly on the solubility of the organic semiconductor materials in conventional solvents and secondly on the low movability, compared to inorganic semiconductors, of the charge carriers, so no particular measures are required to delimit individual light-sensitive regions from one another. These light-sensitive regions are determined by the intersecting strip conductors of the translucent electrode layers, because the conveyance of charge is substantially restricted to the region of intersection of the strip conductors and the influence of a charge movement between adjacent regions of intersection of the strip conductors within the photoactive layer can generally be disregarded. Although differing organic semiconductors can be used, two molecular components are preferably used for the photoactive layer, namely a conjugated polymer component as the electron donor and a fullerene component as the electron acceptor.

If the light-emitting layer is divided into individual regions, each of which can be activated independently, the excitation energy required for the light emission can, first of all, be kept low because the fingerprint is, after all, illuminated merely in certain regions at successive intervals of time. The illumination of the fingerprint in certain regions also allows merely the light reflected by the fingerprint, and not the emitted light, to be detected. For this purpose, not those regions of the photoactive layer that are passed through by the emitted light, but rather the adjacent regions acted on merely by the reflected light, are read out for the evaluation. If the electrical signals from both the regions through which the emitted light shines and the regions acted on by the reflected light are evaluated, the basic loading of the photoactive layer by the emitted light is to be taken into account in order to record the fingerprint based on the differences measured relative to these basic loads.

The light-emitting layer can be constructed from electroluminescent diodes using thin-layer technology. However, particularly advantageous design conditions are obtained if the light-emitting layer has a photoactive layer based on an organic semiconductor between two electrode layers consisting of intersecting strip conductors, of which the electrode layer between the photoactive layer and the layer of light-sensitive elements is translucent at least in certain regions. In this case, similar advantages with regard to the construction and the activation of the light-emitting layer are obtained to those in the layer of light-sensitive elements.

If a respective photoactive layer is used for the light-sensitive and the light-emitting layer, the electrode layers can be separated from one another by an insulating layer on the mutually facing sides of the two photoactive layers. However, it is also possible to provide for the photoactive layer of the light-sensitive layer and the photoactive layer of the light-emitting layer a common electrode layer consisting of parallel strip conductors between the two photoactive layers, and this simplifies the design.

If the photoactive layer of the layer of light-sensitive elements is activated via a control means as a function with respect to time of the activation of the light-emitting layer, the detection of the light transmitted through the light-sensitive elements can also be eliminated for recording the fingerprint, if the dependency with respect to time of the reading-out of the state of excitation of the individual light-sensitive regions of the photoactive layer on the activation of the light-emitting layer is chosen in such a way that not the transmitted light, but rather only the light reflected on the fingerprint is evaluated.

BRIEF DESCRIPTION OF THE DRAWINGS

The drawings show the subject-matter of the invention by way of example. In the drawings.

DESCRIPTION OF THE PREFERRED EMBODIMENT

Figure 2:
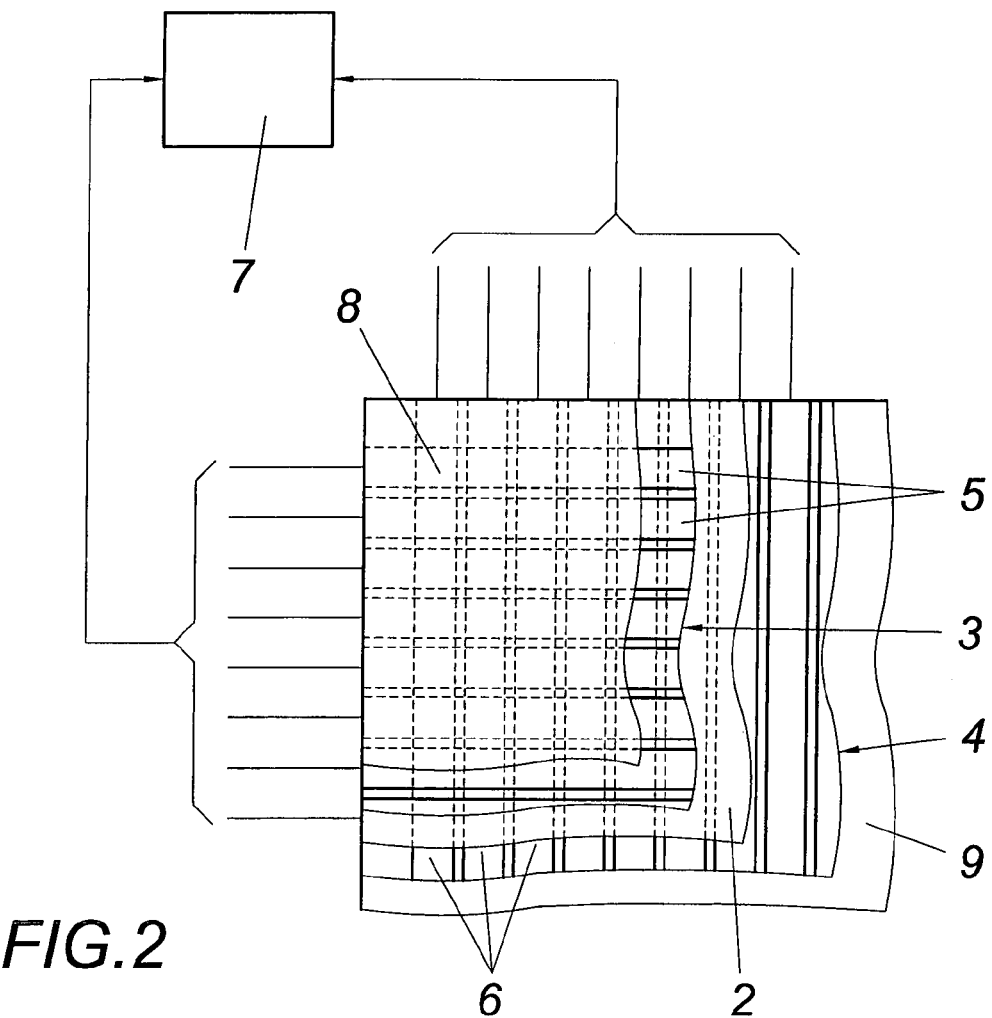
FIG. 2 is a schematic, partially exploded plan view of the device shown in FIG. 1.

According to the illustrated embodiment, the fingerprinting device has a layer 1 of light-sensitive elements in the form of a translucent, photoactive layer 2 consisting, for example, of two molecular organic components, namely a conjugated polymer component as the electron donor and a fullerene component as the electron acceptor. This photoactive layer is provided between electrode layers 3, 4 consisting of intersecting strip conductors 5, 6 connected to an evaluation circuit 7, as indicated in FIG. 2. The strip conductors 5 of the electrode layer 3, acting as a hole-collecting cathode, advantageously consist of an indium/tin oxide (ITO), whereas the electrode layer 4 has aluminum strip conductors as the electron-collecting electrode. Polymer layers can additionally be provided between these electrode layers 3 and 4 and the photoactive layer 2 for improving the hole or electron transfer. The photoactive layer 2 with the electrode layers 3, 4 is attached to a translucent top layer 8 which at the same time forms a finger rest. On the side of the layer 1 of light-sensitive elements that is remote from the top layer 8, there is provided a light-emitting layer 9 which can be constructed, for example, from organic light-emitting diodes or electroluminescent diodes.

Figure 1:
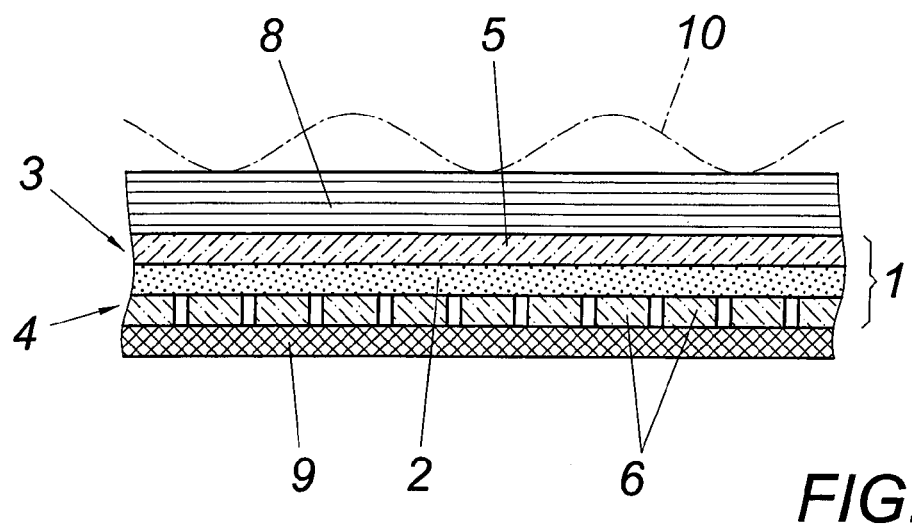
FIG. 1 is a schematic cross section of a fingerprinting device.

In order to record the ridges in the skin, separated from one another by groove-like recesses, of a fingerprint 10 indicated by a dot-dash line in FIG. 1, the light-emitting layer 9 is excited. The emitted light penetrates the translucent layer 1 of light-sensitive elements and also the top layer 8 and is reflected on the fingerprint 10 of the finger resting against the top layer 8 in order to act on the layer 1 of light-sensitive elements. If the arrangement is made in such a way that the light-sensitive elements, which are determined in the photoactive layer 2 by the regions of intersection of the strip conductors 5 and 6, are acted on both by the emitted light for illuminating the fingerprint 10 and by the light reflected on the fingerprint 10, as is the case for example when the illumination covers the entire area, the basic loading, provided by the emitted light, of the light-sensitive elements is to be taken into account in the evaluation of the electrical signals, so merely the resultant differences in the electrical signals relative to these basic loads can be utilised for recording the fingerprint 10. If merely the acting of the reflected light on the light-sensitive elements is to be evaluated for recording the fingerprint 10, there are two options. Either merely certain regions of the fingerprint 10 can be illuminated at successive intervals of time, in order to detect the reflected light via the light-sensitive elements in adjoining regions, or the emitting of the light and the reception of the reflected light can be staggered with respect to time, so the light-sensitive elements are read out after the emission of light has been completed, during the reception of the reflected light. For the activation, in certain regions, of the light-emitting layer 9, the layer 9 is to be constructed and activated accordingly, wherein the layer 9, like the layer 1 of light-sensitive elements, can have a photoactive layer based on organic semiconductors between two electrode layers consisting of intersecting strip conductors, in the region of intersection of which there are provided the light-emitting elements which can be activated individually. Via the strip conductors, individual light-emitting elements can thus be selected and supplied with electrical power for emitting light radiation. As a function of the selection of the light-emitting elements, individual light-sensitive elements of the layer 1 can then be read out into the evaluation circuit 7 for recording the fingerprint 10.

The invention claimed is:

1. Fingerprinting device with a translucent top layer which forms a finger rest and between which and a light-emitting layer a layer of light-sensitive elements is provided in a matrix arrangement, and with an evaluation circuit connected to the light-sensitive elements, wherein the layer of light-sensitive elements has a translucent, photoactive layer based on organic semiconductors between two translucent electrode layers consisting of intersecting strip conductors.

2. Device according to claim 1, wherein the light-emitting layer is divided into individual regions, each of which can be activated independently.

3. Device according to claim 2, wherein the light-emitting layer has a photoactive layer based on an organic semiconductor between two electrode layers consisting of intersecting strip conductors, of which the electrode layer between the photoactive layer and the layer of light-sensitive elements is translucent at least in certain regions.

4. Device according to claim 3, wherein the photoactive layer of the layer of light-sensitive elements and the photoactive layer of the light-emitting layer have between them a common electrode layer.

5. Device according to claim 1, wherein the photoactive layer of the layer of light-emitting elements can be activated via a control means as a function with respect to time of the activation of the light-emitting layer.

* * * * *